United States Patent
Chow et al.

(10) Patent No.: US 7,709,029 B2
(45) Date of Patent: May 4, 2010

(54) CALCIUM-CONTAINING RESTORATION MATERIALS

(75) Inventors: Laurence C. Chow, Germantown, MD (US); Shozo Takagi, Gaithersburg, MD (US)

(73) Assignee: ADA Foundation, Chicago, IL (US)

( * ) Notice: Subject to any disclaimer, the term of this patent is extended or adjusted under 35 U.S.C. 154(b) by 452 days.

(21) Appl. No.: 10/552,337

(22) PCT Filed: Mar. 11, 2004

(86) PCT No.: PCT/US2004/007422

§ 371 (c)(1),
(2), (4) Date: Jul. 21, 2006

(87) PCT Pub. No.: WO2004/093734

PCT Pub. Date: Nov. 4, 2004

(65) Prior Publication Data

US 2006/0263443 A1   Nov. 23, 2006

Related U.S. Application Data

(63) Continuation-in-part of application No. 10/057,554, filed on Jan. 23, 2002, now Pat. No. 6,793,725.

(60) Provisional application No. 60/461,338, filed on Apr. 8, 2003, provisional application No. 60/263,894, filed on Jan. 24, 2001.

(51) Int. Cl.
*A61K 37/42* (2006.01)

(52) U.S. Cl. .......................... 424/602; 106/35; 106/691

(58) Field of Classification Search ................. 106/35, 106/691; 424/602
See application file for complete search history.

(56) References Cited

U.S. PATENT DOCUMENTS

| 4,902,649 | A | 2/1990 | Kimura et al. | |
|---|---|---|---|---|
| 6,793,725 | B2 * | 9/2004 | Chow et al. | 106/35 |
| 6,949,251 | B2 * | 9/2005 | Dalal et al. | 424/423 |
| 7,018,460 | B2 * | 3/2006 | Xu et al. | 106/35 |
| 2002/0137812 | A1 * | 9/2002 | Chow et al. | 523/115 |

FOREIGN PATENT DOCUMENTS

| EP | 0520690 | | 12/1992 |
|---|---|---|---|
| EP | 0538913 | | 4/1993 |
| EP | 0639366 | | 2/1995 |
| JP | 02311406 | * | 5/1989 |
| JP | 2311406 | | 12/1990 |
| JP | 2001170161 | | 6/2001 |

OTHER PUBLICATIONS

Supplementary European Search Report dated Dec. 12, 2008, Application No. 04719777.7, 3 pages.

* cited by examiner

*Primary Examiner*—Ralph Gitomer
(74) *Attorney, Agent, or Firm*—Banner & Witcoff, Ltd.

(57) ABSTRACT

A bone or dental implant material in the form of a paste includes a mixture of calcium phosphate and/or calcium-containing powders, liquid glycerol, organic acid and gelling agent. The paste is stable, resistant to washout and will harden upon exposure to water. Physical characteristics of the paste, including consistency, porosity, and hardening time, are controlled by the choice and ratio of constituents.

9 Claims, No Drawings

CALCIUM-CONTAINING RESTORATION MATERIALS

CROSS-REFERENCE TO RELATED APPLICATIONS

This international application is a continuation-in-part of U.S. application Ser. No. 10/057,554, filed Jan. 23, 2002, now U.S. Pat. No. 6,793,725, which claims the benefit of U.S. Provisional Patent Application Ser. No. 60/263,894, filed on Jan. 24, 2001. This application also is based on and claims the benefit of co-pending U.S. Provisional Patent Application Ser. No. 60/461,338, filed on Apr. 8, 2003, which is incorporated herein by reference.

STATEMENT REGARDING FEDERALLY SPONSORED RESEARCH OR DEVELOPMENT

This development was supported in part by USPHS Research Grant DE11789 to the American Dental Association Health Foundation from the NIDCR. The United States or an agency thereof may have certain rights to the claimed invention.

BACKGROUND OF THE INVENTION

The various embodiments of the present invention are generally directed to self-hardening calcium phosphate-containing and/or calcium-containing cement compositions. The compositions may be used to form pastes for bone and tooth restoration and similar applications, where the paste will harden within a desired time after being delivered to a repair site.

Most conventional calcium phosphate cements are mixed with an aqueous solution immediately before application. In the clinical situation, the ability of the surgeon to properly mix the cement and then place the cement paste in the defect within the prescribed time is a crucial factor in achieving optimum results.

A self-hardening calcium phosphate cement ("CPC"), consisting of tetracalcium phosphate ($Ca_4(PO_4)_2O$, also referred to as "TTCP") and dicalcium phosphate anhydrous ($CaHPO_4$, also referred to as "DCPA"), has been shown in clinical studies to be efficacious for repairing bone defects. The hardening time of such conventional cements is as long as about 30 minutes with water, although hardening time can be shortened if a phosphate solution is used as the cement liquid. Hydroxyapatite ($Ca_5(PO_4)_3OH$, also referred to as "HA") is formed as the product. More recently, additional CPCs that do not contain TTCP, e.g., α-tricalcium phosphate (α-$Ca_3(PO_4)_2$, also referred to as "α-TCP") and $CaCO_3$ or DCPA and $Ca(OH)_2$, have also been developed. These cements may harden in about 10 minutes when a phosphate solution is used as the cement liquid. They also form hydroxyapatite ("HA") as the final product.

A premixed CPC paste containing the TTCP and DCPA powders and glycerol as the cement liquid has been used for root canal filling and sealing by injection techniques. The cement paste was found to be stable in a syringe but hardened only after being delivered into the root canal where it became exposed to water from the surrounding tissues. Because the cement paste was injected into a confined area, there was little concern of disintegration of the paste due to washout. Although the premixed CPC was shown to have improved biocompatibility with periapical bone tissue than a number of conventional root canal filling or sealing materials, the premixed CPC-glycerol paste did not exhibit a good washout resistance when it was applied to an open wet field.

There remains a need for premixed cement pastes that are stable in the package, are resistant to washout, and will harden only after being deposited at the site of the defect but, once placed, will then harden within a predetermined time.

BRIEF SUMMARY OF THE INVENTION

The various embodiments of the present invention comprise compositions and means for formulating premixed calcium and/or calcium phosphate and organic acid cement pastes that are stable in a package, resistant to washout, and harden within a desired time after being delivered to the defect or implant site. A non-toxic, non-aqueous, water-miscible liquid such as gycerol is preferred as the liquid in the premix because the cement paste hardening reaction to form calcium complexes and HA does not occur in a water-free environment. An organic acid is used to accelerate cement hardening upon delivery to a desired repair site. Preferred organic acids include carboxylic acids. A gelling agent also may be added to improve the paste cohesiveness.

Methods of repairing and restoring bone and tooth tissue include delivering the pastes to the defect site by any suitable methods known to those of skill in the art. The pastes are exposed to an aqueous fluid to promote hardening of the paste to a cement at a relatively rapid rate.

When premixed self-hardening cements are formulated with sodium phosphate ("$Na_2HPO_4$") to accelerate cement hardening and prepared by mixing glycerol, $Na_2HPO_4$, and hydroxypropyl methyl cellulose ("HMC") with CPC powders, the cements will harden only after being delivered to a desired site. Although $Na_2HPO_4$ may serve to accelerate cement hardening, the hardening times ("HT") of these cements can be 60 minutes or longer. Where shorter hardening times are desired, the present compositions that include organic acids to accelerate cement hardening provide self-hardening calcium phosphate-containing and/or calcium-containing cement pastes having hardening times of about 35 minutes or less.

Thus, it is an object of the invention to provide a premixed composition of a calcium phosphate-containing and/or calcium-containing cement material which exhibits resistance to washout as well as desirable hardening times.

A further object of the invention is to provide an essentially water-free, cement-forming paste capable of forming calcium complexes and HA after exposure to water for repair of dental material and bone.

Another object of the invention is to provide a method for controlling the hardening times of HA forming cements pastes.

Another object of the invention is to provide an HA forming cement formulation capable of remaining in an injectable paste form until exposed to an aqueous environment. These and other objects, advantages and features of the invention are set forth in the detailed description which follows.

DETAILED DESCRIPTION OF THE INVENTION

Premixed calcium cement pastes for use in bone graft and similar medical repair applications are provided. The pastes may be injectable for delivery to the bone or tooth defect site. The pastes may include a non-toxic, calcium-containing and/or calcium phosphate-containing powder, a non-toxic organic acid capable of forming calcium complexes, and a non-toxic, non-aqueous, water-miscible liquid. Non-aqueous liquids are preferred to limit premature hardening of the pastes, which may harden in aqueous environments. A preferred liquid is glycerin (also sometimes referred to as "glycerol"). The organic acid is used to accelerate the hardening time of the paste upon delivery. Gelling agents, such as HMC, carboxymethyl cellulose ("CMC"), alginate, chitosan, and the like, also can be mixed with the powders to enhance paste cohesiveness and washout resistance.

Because the hardening of these cements results from calcium-complex formation, it is contemplated that self-hardening cements can also be formulated using calcium-containing compounds instead of, or in combination with, calcium phosphate compounds. The calcium phosphate and/or calcium-containing compound powder can include monocalcium phosphate monohydrate ("MCPM"), monocalcium phosphate anhydrous ("MCPA"), dicalcium phosphate anhydrous ("DCPA"), dicalcium phosphate dehydrate ("DCPD"), octacalcium phosphate ("OCP"), α-TCP, β-tricalcium phosphate ("β-TCP"), amorphous calcium phosphate ("ACP"), calcium deficient HA, non-stoichiometric HA, TTCP, $CaSO_4$, $CaSO_4.0.5\ H_2O$, $CaSO_4.2\ H_2O$, CaO, $Ca(OH)_2$, and $CaCO_3$ and combinations thereof. Preferred calcium phosphate powders include TTCP, DCPA, α-TCP and β-TCP. The Ca/P molar ratio of TTCP is preferably between about 1.67 to about 2, of α-TCP is between about 1.5 to about 1.67, and of β-TCP is between about 1.50 to about 1.67. The particle sizes of the calcium phosphate and/or calcium-containing compounds are between about 1 to about 200 μm and more preferably between about 2 to about 50 μm.

Any suitable, non-toxic, non-aqueous, water-miscible liquid may be used in preparing the pastes. Possible liquids include glycerin, as well as related liquids, such as glycerin compounds, derivatives, substitutes and the like, that are non-toxic, non-aqueous, and water-miscible. Certain alcohols also may be suitable for use as the non-toxic, non-aqueous, water-miscible liquid. Preferably, the liquid is selected from glycerin, propylene glycol, poly(propylene glycol), poly(ethylene glycol), and combinations thereof.

Preferred organic acids are non-toxic, organic carboxylic acids. A number of carboxylic acids form calcium complexes that are not highly soluble. These acids include glycolic, citric, tartaric, malonic, malic, and maleic acids. Some of these acids, when mixed with a powder containing one or more of calcium phosphate compounds and/or calcium-containing compounds produce relatively fast hardening cements. Thus, it is possible that the use of these acids can produce faster setting premixed cements. One or more of these acids are mixed with the powder to provide a stable paste that will harden only upon contact with an aqueous fluid. Without wishing to be bound by any theories, it is believed that the calcium phosphate compounds and/or calcium-containing compounds react with the organic acids in the presence of water to initially form calcium complexes that are not highly soluble, rather than to directly form hydroxyapatite. This then results in more rapid hardening of the paste.

The compositions also may include a non-toxic gelling agent to enhance paste cohesiveness and washout resistance. The gelling agent may include HMC, CMC, chitosan, collagen, gum, gelatin, and alginate, and combinations thereof.

The compositions are prepared and stored under substantially anhydrous conditions to limit premature hardening of the cement pastes. The compositions may be employed as self-hardening cement pastes in a variety of medical and dental procedures for repairing or restoring missing or defective bone or tooth tissue. The cement pastes may be applied to the defect site using any suitable methods, including injecting with a syringe or depositing with a spatula, and also molded or sculpted in vivo as desired. When the cement pastes are exposed to physiologic fluids, which contain water, or another aqueous environment at the defect site, they will harden relatively rapidly. An aqueous fluid may be contacted with the compositions either prior to or after application of the cement pastes at the defect site to enhance the rate of hardening of the cement pastes. As an example, a sodium phosphate or saline solution may be sprayed over the surface of the cement paste after it is delivered to the defect site to promote hardening of the outer surface of the cement paste, which will also assist with maintaining the shape of the cement paste as applied and molded. As another example, water may be mixed with the cement pastes prior to application of the pastes at the defect site to initiate hardening.

For most clinical applications, a cement hardening time of more than 60 minutes is too long. Premixed pastes or self-hardening bone graft pastes ("BGPs") in accordance with the various embodiments of the present invention will have an HT of no more than about 35 minutes, preferably no more than 20 minutes and even more preferably between about 5 to about 15 minutes.

EXAMPLES

The following examples further illustrate preferred embodiments of the present invention but are not be construed as in any way limiting the scope of the present invention as set forth in the appended claims.

Various premixed self-hardening pastes were prepared. Hardening times and other properties of the pastes were evaluated.

Preparation of the solid ingredients of premixed paste: TTCP was prepared by heating an equimolar mixture of commercially obtained DCPA (Baker Analytical Reagents, J.T. Baker Chemical Co., Phillipsburg, N.J.) and $CaCO_3$ (J.T. Baker Chemical Co.) at 1500° C. for 6 hours in a furnace and quenched at room temperature. The TTCP and DCPA powders of the paste compositions were ground individually in a planetary ball mill in cyclohexane, ethanol, or without a liquid to obtain the desired median particle sizes, which typically is about 15 μm as disclosed in the prior art for making CPC powders. The median particle sizes of TTCP and DCPA were about 17.1 μm and about 1.7 μm, respectively.

α-TCP was prepared by heating a mixture that contained 2 mol of DCPA and 1 mol of $CaCO_3$ to 1500° C. for 6 hours and then quenched in air. The powders were ground individually in a planetary ball mill in cyclohexane, ethanol, or without a liquid to obtain the desired median particle sizes based on data from previous studies. The median particle sizes of α-TCP and $CaCO_3$ were 4.6 μm and 3.9 μm, respectively. The median particle size of $Ca(OH)_2$ was 2.2 μm. The particle sizes of the components of the pastes prepared in accordance with the present invention generally can be in the range of 1 to 50 μm.

Liquid ingredients of controls and premixed pastes: All ingredients were obtained commercially. A homogeneous mixture of a carboxylic acid, HMC or CMC, and glycerin was produced by blending the mixture in a ball mill.

Preparation of premixed pastes: Premixed paste compositions were prepared by mixing a powder and a liquid at desired powder-to-liquid mass ratios (P/L) on a mixing block until a smooth and homogenous paste was obtained. The compositions, with components expressed in mass fraction (%) are presented in Table 1.

TABLE 1

| Paste | Solid | Liquid | | | P/L |
|---|---|---|---|---|---|
| | | Glycerin | Carboxylic Acid | Gelling Agent | |
| P1 | TTCP (73%) DCPA (27%) | 62.2% | d-tartaric acid (37.5%) | HMC (0.3%) | 3.0 |
| P2 | TTCP (73%) DCPA (27%) | 62.2% | glycolic acid (37.5%) | HMC (0.3%) | 3.0 |
| P3 | TTCP (73%) DCPA (27%) | 70.5% | malonic acid (29%) | HMC (0.5%) | 3.0 |
| P4 | TTCP (73%) DCPA (27%) | 79.5% | maleic acid (20%) | HMC (0.5%) | 3.0 |
| P5 | TTCP (73%) DCPA (27%) | 49.3% | citric acid (49.2%) | CMC (1.5%) | 2.3 |
| P6 | TTCP (39.1%) α-TCP (60.9%) | 61.9% | d-tataric acid (37.1%) | CMC (1%) | 1.5 |
| P7 | TTCP (55%) DCPA (20%) α-TCP (25%) | 61.9% | d-tataric acid (37.1%) | CMC (1%) | 1.5 |
| P8 | TTCP | 61.9% | d-tataric acid (37.1%) | CMC (1%) | 1.5 |
| P9 | α-TCP | 61.9% | d-tataric acid (37.1%) | CMC (1%) | 1.5 |

Washout resistance test: The washout resistance of the premixed pastes was tested as follows. Premixed paste samples were shaped into a small sphere by hand, and then placed immediately in a 5 mL of physiologic-like solution ("PLS") (1.15 mM Ca, 1.2 mM P, 133 mM NaCl, 50 mM HEPES, pH=7.4) at 37° C. The sample was considered to pass the washout resistance test if it did not visibly disintegrate in the PLS. All samples exhibited excellent washout resistance.

Diametral tensile strength ("DTS") measurement: DTS samples were prepared by placing the premixed paste into a mold (6 mm diameter by 3 mm height) with about 2 MPa of applied pressure. The mold was covered with two fritted glass slides (pore size of about 40 μm to about 60 μm, thickness of about 3.5 mm) and immersed in PLS at 37° C. Glycerol-PLS exchange occurred through the fritted glass, allowing the paste to harden. Samples were removed from molds at about 4 hours, and then each sample was immersed in 30 mL of PLS for an additional 20 hours. In some cases, additional samples were prepared and samples were immersed in PLS for an additional 6 days with the PLS being changed daily (30 mL/specimen at 37° C.) to investigate the effect of PLS immersion on physicochemical properties. DTS values (standard uncertainty equals 5%) were measured on a Universal Testing Machine (United Calibration Corp, Garden Grove, Calif.) using a loading rate of 10 mm/min, Hardening time measurements: The Gilmore needle method (standard uncertainty equals 5%) was used to measure hardening time on samples prepared as described above for DTS measurements. All samples exhibited short hardening times. The hardening times were as shown in Table 2.

TABLE 2

| Premixed Paste | HT (minutes, mean ± standard deviation, n = 3) |
|---|---|
| P1 | 10 ± 1 |
| P2 | 15 ± 1 |
| P3 | 20 ± 1 |
| P4 | 20 ± 1 |
| P5 | 35 ± 1 |
| P6 | 15 ± 1 |
| P7 | 25 ± 1 |
| P8 | 35 ± 1 |
| P9 | 20 ± 1 |

Assessments of hydroxyapalite formation: Powder X-ray diffraction ("XRD") analysis was used to estimate the extent of paste conversion to HA. The estimated standard uncertainty in 2θ measurements is 0.01° and the minimum mass fraction of a calcium phosphate phase that can be detected by XRD is about 3%.

Diametral Tensile (DTS) Strength

DTS of some of the premixed paste samples were determined as given in Table 3.

TABLE 3

| Paste | 1-day DTS (MPa) | 7-day DTS (MPa) |
|---|---|---|
| P1 | 4.3 ± 0.3 (n = 5) | 3.8 ± 0.3 |
| P2 | 3.1 ± 0.5 | 3.0 ± 0.3 |
| P3 | 2.3 ± 0.4 | 2.7 ± 0.3 |

Hydroxyapatite ("HA") Formation: Conversion of the initial cement compositions to HA was incomplete in 1-day samples. Complete and near complete conversion of the initial cement compositions to HA was found in all 7-day samples of premixed pastes using XRD.

In sum, formation of a bone replacement or dental replacement paste results by combining dry powder constituents, characterized by their conversion to calcium complexes in the presence of carboxylic acids and water. A gelling agent, such as hydroxypropyl methyl cellulose, can be mixed with the powder to improve the cohesiveness of the paste. The ratio of combined constituents is broad and the resulting paste can be formulated to control rather precisely the physical properties of the paste, including injectability, porosity and hardening time.

While particular embodiments of the present invention have been described and illustrated, it should be understood that the invention is not limited thereto as modifications may be made by persons skilled in the art. The present application contemplates any and all modifications that fall within the spirit and scope of the underlying invention disclosed herein.

What is claimed is:

1. A self hardening, non-aqueous premixed composition of matter comprising:
   a non-toxic, non-aqueous water-miscible liquid;
   a gelling agent;
   a powdered calcium compound in the form of selectively sized powder particles, said particle size in the range of 1 μm to 50 μm, said particles comprising a calcium compound selected from the group consisting of monocalcium phosphate monohydrate, monocalcium phosphate anhydrous, dicalcium phosphate anhydrous, dicalcium phosphate dehydrate, octacalcium phosphate, α-tricalcium phosphate, β-tricalcium phosphate, amorphous calcium phosphate, calcium deficient hydroxyapatite, non-stoichiometric hydroxyapatite, tetracalcium phosphate, $CaSO_4$, $CaSO_4 \cdot 0.5 \ H_2O$, $CaSO_4 \cdot 2 \ H_2O$, CaO, $Ca(OH)_2$, $CaCO_3$ and mixtures thereof; and
   a carboxylic acid for accelerating hardening of said composition when said composition is exposed to water at a delivery site, said acid comprising an acid selected from the group consisting of glycolic, citric, tartaric, malonic, malic, and maleic acids and combinations thereof;
   said composition being substantially an anhydrous paste and which forms a self hardening bone and tooth restoration material upon further contact with an aqueous material having a hardening time of less than about 35 minutes and a diametral tensile strength (DTS) greater than 2.7 MPa within 7 days after hardening.

2. The composition of claim 1, wherein the gelling agent is selected from the group consisting of hydroxy methyl, cellulose, carboxymethyl cellulose, chitosan, collagen, gum, gelatin, and alginate, and combinations thereof.

3. The composition of claim 1, wherein the liquid comprises glycerin.

4. A composition according to claim 1, said composition comprising a bone graft paste having a hardening time of no more than 20 minutes when exposed to an aqueous environment at a delivery site.

5. A composition according to claim 1, said composition comprising a bone graft paste having a hardening time between about 5 to about 15 minutes when exposed to an aqueous environment at a delivery site.

6. A composition according to claim 1, said miscible liquid being selected from the group consisting of propylene glycol, poly(propylene glycol), poly(ethylene glycol) and mixtures thereof.

7. The composition of claim 1 wherein the powder particle to liquid ratio of constituents is in the range of about 1.5 to 3.0.

8. The composition of claim 1 wherein the powder particle size is in the range of about 1 μm to 50 μm, the hardening time upon mixing with an aqueous source is less than about 35 minutes and the powdered calcium compound comprises at least about 60% of the mass of the composition.

9. A self hardening, non-aqueous premixed composition of matter comprising:
- a non-toxic, non-aqueous water-miscible liquid selected from the group consisting of propylene glycol, poly(ethylene glycol), poly(ethylene glycol) and mixtures thereof;
- a gelling agent selected from the group consisting of hydroxyl methyl cellulose, carboxymethyl cellulose, chitosan, collagen, gum, gelatin, alginate and combinations thereof;
- a powdered calcium compound in the form of selectively sized powder particles said powder particles having a size in the range of about 1 μm to 50 μm and selected from the group consisting of monocalcium phosphate monohydrate, monocalcium phosphate anhydrous, dicalcium phosphate anhydrous, dicalcium phosphate dehydrate, octacalcium phosphate, α-tricalcium phosphate, β-tricalcium phosphate, amorphous calcium phosphate, calcium deficient hydroxyapatite, non-stoichiometric hydroxyapatite, tetracalcium phosphate, $CaSO_4$, $CaSO_4.0.5 H_2O$, $CaSO_4.2 H_2O$, $CaO$, $Ca(OH)_2$, $CaCO_3$ and mixtures thereof; and
- a carboxylic acid for accelerating hardening of said composition when said composition is exposed to water at a delivery site, said acid selected from the group consisting of glycolic, citric, tartaric, malonic, malic, and maleic acids and combinations thereof,
- said composition being substantially an anhydrous paste and has a the hardening time upon mixing with an aqueous source being less than about 35 minutes and the powdered calcium compound comprising at least about 60% of the mass of the paste composition.

* * * * *